(12) United States Patent
Yajima et al.

(10) Patent No.: US 7,179,354 B2
(45) Date of Patent: Feb. 20, 2007

(54) ELECTROCHEMICAL SENSOR

(75) Inventors: Tatsuhiko Yajima, Honjo (JP); Shunichi Uchiyama, Fukaya (JP); Shinichi Harima, Fujimi (JP)

(73) Assignee: Tanita Corporation, Tokyo (JP)

( * ) Notice: Subject to any disclaimer, the term of this patent is extended or adjusted under 35 U.S.C. 154(b) by 698 days.

(21) Appl. No.: 10/430,301

(22) Filed: May 7, 2003

(65) Prior Publication Data

US 2003/0217919 A1 Nov. 27, 2003

(30) Foreign Application Priority Data

May 21, 2002 (JP) ............................. 2002-145586
Feb. 27, 2003 (JP) ............................. 2003-050297

(51) Int. Cl.
*G01N 27/333* (2006.01)
*G01N 27/401* (2006.01)

(52) U.S. Cl. ...................... 204/422; 204/418; 204/433

(58) Field of Classification Search ........ 204/416–418, 204/419–421, 433
See application file for complete search history.

(56) References Cited

U.S. PATENT DOCUMENTS

| | | | | |
|---|---|---|---|---|
| 4,454,007 A | * | 6/1984 | Pace | 205/778 |
| 4,559,112 A | | 12/1985 | Tamamura et al. | |
| 4,582,589 A | | 4/1986 | Ushizawa et al. | |
| 5,110,441 A | | 5/1992 | Kinlen et al. | |
| 5,354,449 A | | 10/1994 | Band et al. | |

FOREIGN PATENT DOCUMENTS

| | | |
|---|---|---|
| EP | 0 433 261 | 6/1991 |
| JP | 07-128282 | 5/1995 |
| JP | 09-61399 | 3/1997 |
| JP | 09-138215 | 5/1997 |
| JP | 11-258197 | 9/1999 |
| JP | P3390154 | 1/2003 |
| JP | P3390193 | 1/2003 |
| WO | WO 01/64938 A2 | 9/2001 |

OTHER PUBLICATIONS

Excerpt from 5.3.7 Ionomers from "Plastics, General Survey" in Ullmann's Encyclopedia of Industrial Chemistry. online postin date: Jun. 15, 2000.*
"Kinlen P J et al", "A solid-state pH sensor based on a Nafion-coated iridium oxide indicator electrode and a polymer-based silver chloride reference electrode" vol. 22, No. 1, Oct. 1, 1994, pp. 13-25.

* cited by examiner

*Primary Examiner*—Alex Noguerola
(74) *Attorney, Agent, or Firm*—McDermott Will & Emery LLP

(57) ABSTRACT

Disclosed is an electrochemical sensor comprising a work electrode and a reference electrode, said sensor adapted to measure the characteristics of a liquid under test, based on the relative electric potential difference and electric current between the work electrode and the reference electrode both immersed in the liquid under test, said work electrode comprising a substrate that reacts to the liquid under test for generating an electric potential according to the concentration of the liquid under test, and said reference electrode comprising a substrate that reacts to the liquid under test for generating a fixed electric potential. According to the present invention, at least one of the work electrode and the reference electrode comprises said substrate coated with a function film for serving to generate the electric potential through the intervention of the film between said substrate and the liquid under test.

14 Claims, 6 Drawing Sheets

ELECTROCHEMICAL SENSOR

This application claims foreign priority under 35 U.S.C. 119(a–d) from JP 2002-145586, filed May 21, 2002, and JP 2003-050297, filed Feb. 27, 2003.

BACKGROUND OF THE INVENTION

1. Field of the Invention

The present invention relates to an electrochemical sensor comprising a work electrode and a reference electrode, said sensor adapted to measure the characteristics of a liquid under test, based on the relative electric potential difference and electric current between the work electrode and the reference electrode both immersed in the liquid under test as a pair, said work electrode comprising a substrate formed from platinum, gold, platinum black, etc., and said reference electrode comprising a substrate formed from silver coated with silver oxide film or a substrate formed from gold.

2. Prior Art

In a conventional electrochemical sensor, for example, a hydrogen ion concentration (hereafter referred to as "PH") sensor, a work electrode is configured in such manner that a tube filled with a solution at the known PH value as the internal liquid is provided, a substrate forming the work electrode is immersed in the solution within the tube, and one end of the tube positioned adjacent a liquid under test is provided with a thin glass film having hydrogen ion selection capability via which the internal liquid is made contact with the liquid under test. On the other hand, a reference electrode is configured in such manner that a tube filled with a salt bridge solution at neutral ion concentration as the internal reference liquid is provided, a substrate forming the reference electrode is immersed in the solution within the tube, and a portion of the tube immersed in the solution under the test at the time of measurement is provided with a liquid communication section formed from porous ceramic, porous resin, etc., via which the internal reference liquid is made contact with the liquid under test.

One such conventional configuration can be found, for example, in Japanese Patent Laid-Open No. 11-258197 (hereafter referred to as "Patent Literature 1") and it is especially illustrated in FIG. 5 of this patent literature. Referring to correspondence between the names of the components in FIG. 5 of Patent Literature 1 and those of the PH sensor as described above, a glass electrode "a" is the work electrode, a glass electrode body "c" is the tube of the work electrode, a glass electrode internal liquid "f" is the internal liquid, a glass electrode internal pole "e" is the substrate of the work electrode, a response glass "d" is the thin glass film, a comparison electrode "b" is the reference electrode, a comparison electrode body "h" is the tube of the reference electrode, a comparison electrode internal liquid "j" is the internal reference liquid, a comparison electrode internal pole "i" is the substrate of the reference electrode, and a liquid communication member "m" is the liquid communication section.

Furthermore, in an oxidation-reduction potential (hereafter referred to as "ORP") sensor, a work electrode is configured such that a substrate forming it is directly immersed in a liquid under test, which obviates the need for an internal liquid, a glass tube, etc. The reference electrode is, however, configured in the same manner as the PH sensor, as described above.

Moreover, in a PH meter and an ORP meter incorporating the electrochemical sensor configured as described above, an amplifier having higher input impedance is included therein.

Japanese Patent Laid-Open No. 11-258197 (Patent Literature 1) is incorporated herein by reference.

However, the previous PH sensor described above has been suffered from many deficiencies: the sensor is difficult to handle or manufacture because of liquid such as the internal liquid, the internal reference liquid, etc., involved therein; and the sensor is limited in miniaturization of the tube continuously filled with the liquid. In addition, because of necessity to provide one end of the tube with the liquid communication section formed from thin glass film or ceramic, the glass tube capable of connecting under the sintering has been used, but it was very difficult to handle. For the work electrode the thin glass film in contact with the liquid under test is significantly small in thickness and is likely to be broken. For the reference electrode the internal reference liquid tends to slightly leak out via the liquid communication section. Therefore, if no action taken, some crystal of the internal reference liquid with moisture vaporized is deposited on the surface of the liquid communication section, which necessitates cleaning of the surface of the liquid communication section to which the liquid under test is contact, prior to the measurement. Furthermore, in order to replenish the internal reference liquid by an amount of leakage it was necessary to provide any additional source of the internal reference liquid for replenishing. In addition, there was possibility in the liquid communication section that the liquid under test may reversely flow to lower the concentration of the internal reference liquid and to cause any change in potential between the liquids, which leads to measurement error.

The ORP sensor is also difficult to handle and has a limitation in miniaturization because of liquid catalyst used in the reference electrode.

Because the electrode formed from the thin glass film or the liquid catalyst has an increased internal resistance it is necessary to use an amplifier having higher input impedance for increasing the voltage revel for measurement, which adds the cost of the device.

In view of the above an object of the present invention is to provide an electrochemical sensor that obviates the need for the internal liquid by solidifying the electrode using various types of thin films, that is easy to handle, and that has capability of miniaturization.

SUMMARY OF THE INVENTION

In order to attain such object, according to one aspect of the present invention, there is provided an electrochemical sensor comprising a work electrode and a reference electrode, said sensor adapted to measure the characteristics of a liquid under test, based on the relative electric potential difference and electric current between the work electrode and the reference electrode both immersed in the liquid under test, said work electrode comprising a substrate that reacts to the liquid under test for generating an electric potential according to the concentration of the liquid under test, and said reference electrode comprising a substrate that reacts to the liquid under test for generating a fixed electric potential, wherein at least one of the work electrode and the reference electrode comprises said substrate coated with a function film for serving to generate the electric potential through the intervention of the film between said substrate and the liquid under test.

According to another aspect of the present invention, there is provided an electrochemical sensor comprising a work electrode and a reference electrode, said sensor adapted to measure the characteristics of a liquid under test, based on the relative electric potential difference and electric current between the work electrode and the reference electrode both immersed in the liquid under test, said work electrode comprising a substrate formed from platinum, gold, platinum black, etc., and said reference electrode comprising a substrate formed from silver coated with silver chloride film or a substrate formed from gold, wherein said reference electrode comprises said substrate coated with a function film for serving to generate the electric potential through the intervention of the film between said substrate and the liquid under test.

According to one embodiment of the present invention the reference electrode comprises said substrate formed from silver coated with silver chloride film and a salt bridge retaining film provided on said substrate as the function film.

According to another embodiment the reference electrode comprises said gold substrate and a plasma polymerized film having selective material non-transmission capability provided on said gold substrate as the function film, said plasma polymerized film consisting of at least one of aromatic compound, fluorinated compound, alcohol compound, etc.

According to further embodiment the reference electrode comprises said gold substrate and a basic solution immersion film provided on said gold substrate as the function film by immersing the substrate in the basic solution such as sodium hydroxide, potassium hydroxide, etc.

According to yet further embodiment the work electrode comprises said substrate formed from platinum, gold, platinum black, etc., and a plasma polymerized film having selective material transmission capability provided on said substrate, said plasma polymerized film consisting of at least one of aromatic compound, fluorinated compound, alcohol compound, etc.

According to yet further embodiment said selective material transmission capability for said plasma polymerized film of the work electrode provides selective transmission of hydrogen ion.

According to yet further embodiment said work electrode and said reference electrode are coated with a fixed hydrophobic film consisting of alkane polymer and annular olefin polymer.

According to yet further embodiment said work electrode and said reference electrode are integrally assembled, but insulated from each other.

According to yet further embodiment said salt bridge retaining film is a perfluoroalkylsulfonic acid film impregnated with salt bridge of potassium chloride, sodium chloride, etc.

According to yet further embodiment said salt bridge retaining film is a salt bridge crystal film formed by crystallization of salt bridge of potassium chloride, sodium chloride, etc.

According to yet further embodiment said salt bridge is a mixture to which silver chloride is further added.

BRIEF DESCRIPTION OF THE DRAWINGS

The present invention will be described in more detail with reference to the accompanying drawings in which.

DESCRIPTION OF THE PREFERRED EMBODIMENTS

Figure 1:
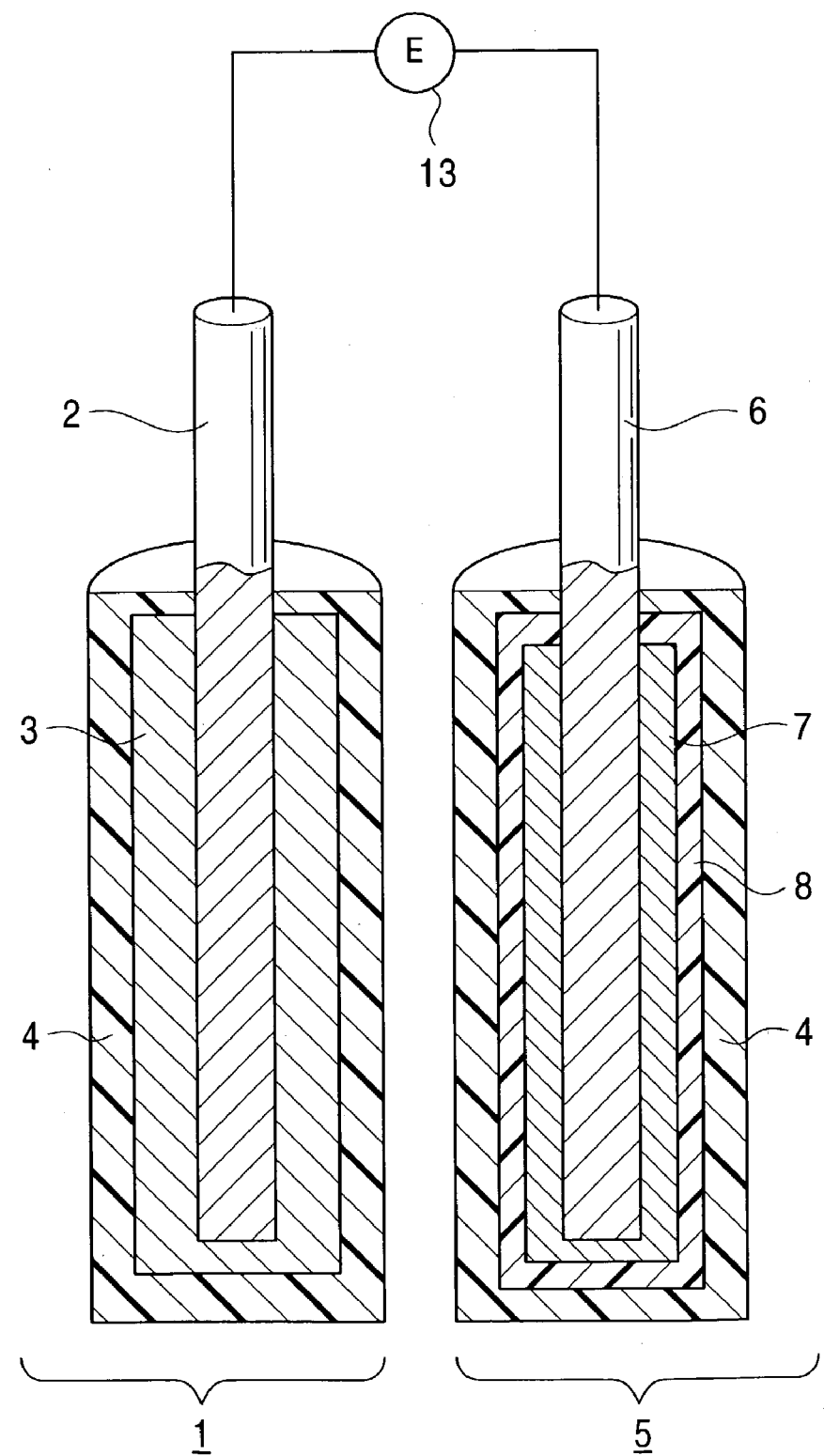
FIG. 1 is a view illustrating a PH sensor according to a first embodiment of the present invention.

The present invention relates to an electrochemical sensor comprising a work electrode and a reference electrode, said sensor adapted to measure the characteristics of a liquid under test, based on the relative electric potential difference and electric current between the work electrode and the reference electrode both immersed in the liquid under test, said work electrode comprising a substrate that reacts to the liquid under test for generating an electric potential according to the concentration of the liquid under test, and said reference electrode comprising a substrate that reacts to the liquid under test for generating a fixed electric potential. According to the present invention at least one of the work electrode and the reference electrode comprises said substrate coated with a function film for serving to generate the electric potential through the intervention of the film between said substrate and the liquid under test. As the result, the present invention advantageously obviates the need of the internal liquid used in the electrochemical sensor, makes easy to manufacture and handle the sensor, and allows for miniaturization of the sensor.

The present invention also relates to an electrochemical sensor comprising a work electrode and a reference electrode, said sensor adapted to measure the characteristics of a liquid under test, based on the relative electric potential difference and electric current between the work electrode and the reference electrode both immersed in the liquid under test, said work electrode comprising a substrate formed from platinum, gold, platinum black, etc., and said reference electrode comprising a substrate formed from silver coated with silver chloride film or a substrate formed from gold. According to the present invention said reference electrode comprises said substrate (i.e., the substrate formed from silver coated with silver chloride film or the substrate formed from gold) coated with a function film for serving to generate the electric potential through the intervention of the film between said substrate and the liquid under test. As the result, the present invention makes easy to manufacture and handle the electrochemical sensor, and allows for miniaturization of the sensor.

Furthermore, the present invention relates to an electrochemical sensor comprising a work electrode and a reference electrode, said sensor adapted to measure the characteristics of a liquid under test, based on the relative electric potential difference and electric current between the work electrode and the reference electrode both immersed in the liquid under test, said work electrode comprising a substrate formed from platinum, gold, platinum black, etc., and said reference electrode comprising a substrate formed from silver coated with silver chloride film. According to the present invention the reference electrode comprises said substrate coated with a salt bridge retaining film (in more specifically, the reference electrode comprises said substrate formed from silver coated with silver chloride film and a salt bridge retaining film provided on said substrate as the function film). Such configuration of the present invention advantageously obviates the need of the internal liquid and makes possible for solidification of the electrode. As the result, the precision in measurement is enhanced because of no change in voltage between the liquids. In addition, handling of the electrochemical sensor is facilitated and miniaturization of the sensor becomes possible.

Alternatively, the reference electrode may comprise said gold substrate and a plasma polymerized film having selective material non-transmission capability provided on said gold substrate as the function film, said plasma polymerized film consisting of at least one of aromatic compound, fluorinated compound, alcohol compound, etc. As the result, advantageously the internal liquid is unnecessary and the solidification of the electrode becomes possible. In addition, the precision in measurement is enhanced because of no change in voltage between the liquids. Moreover, handling of the electrochemical sensor is facilitated and miniaturization of the sensor becomes possible.

Furthermore, the reference electrode may comprise said gold substrate and a basic solution immersion film provided on said gold substrate as the function film by immersing the substrate in the basic solution such as sodium hydroxide, potassium hydroxide, etc. Accordingly, the internal liquid is unnecessary and the solidification of the electrode becomes possible. The precision in measurement is enhanced because of no change in voltage between the liquids. Moreover, handling of the electrochemical sensor is facilitated and miniaturization of the sensor becomes possible.

In the electrochemical sensor of the present invention the electrode is solidified using the coating of thin films. Therefore, as compared to the electrode using the thin glass film or the liquid catalyst, the internal resistance of the electrode becomes reduced, which obviates need of the amplifier having higher input impedance for increasing the voltage level upon measuring the potential difference. Accordingly, it is possible to measure with an inexpensive measuring device incorporating a common potentiometer.

Furthermore, work electrode may comprise said substrate formed from platinum, gold, platinum black, etc., and a plasma polymerized film having selective material transmission capability provided on said substrate, said plasma polymerized film consisting of at least one of aromatic compound, fluorinated compound, alcohol compound, etc. In particular, said selective material transmission capability for said plasma polymerized film of the work electrode allows selective transmission of hydrogen ion. Accordingly, if, for example, paraxylene, an aromatic compound, is applied to the substrate using the plasma polymerization process, it is possible to form a film having the capability of selectively transmitting hydrogen ion. In addition, this plasma polymerized film is advantageous in that it has higher close adhesion to the substrate, it prevents any bubble from mixing or any liquid under test from entering, and it removes any other material than hydrogen ion in the liquid under test. If the combination of said compounds or the condition for plasma polymerization is changed it is possible to form any plasma polymerized film suitable for selectively transmitting any specific material of each type. Alternatively, if a plurality of plasma polymerized films each having different characteristic are formed in parallel on the substrate, a plurality of liquid characteristics may be measured.

The work electrode and the reference electrode may be coated with a fixed hydrophobic film consisting of alkane polymer and annular olefin polymer. In such case, because of suppression in peering of thin film and increase in strength, the service life of the electrode is extended.

Furthermore, the work electrode and the reference electrode may be integrally assembled, but insulated from each other. Therefore, further miniaturization of the electrochemical sensor of the present invention may be possible. In addition, because of close proximity of both electrodes, the internal resistance in the measuring system is minimized.

Moreover, the salt bridge retaining film may be a perfluoroalkylsulfonic acid film impregnated with salt bridge of potassium chloride, sodium chloride, etc., or may be a salt bridge crystal film formed by crystallization of salt bridge of potassium chloride, sodium chloride, etc. In this case, any thin film retaining the salt bridge therein reaches an electrical equilibrium with the liquid under test through chlorine ion in salt bridge in the thin film. Accordingly, the liquid under test is prevented from contacting to the substrate for erosion thereto, which makes possible to extend the service life of the sensor.

Furthermore, the salt bridge may be a mixture to which silver chloride is further added. In such case, the substrate may simply be formed from silver without any silver chloride coating.

Now, a first embodiment of an electrochemical sensor according to the invention will be described with reference to a galvanic PH meter.

FIG. 1 is a view illustrating a PH sensor (or a galvanic PH meter) according to a first embodiment of the present invention. The PH sensor comprises a work electrode 1 and a reference electrode 5. The work electrode 1 includes a substrate 2 formed from a platinum black wire; a plasma polymerized film 3 having capability of selectively transmitting hydrogen ion provided on the surface of the substrate 2; and a fixed hydrophobic film 4 for protecting and stabilizing the plasma polymerized film 3 on the substrate 2.

The plasma polymerized film 3 is a thin film having the thickness of a few tens nm and formed from paraxylene, an aromatic compound, using the plasma polymerization process. The fixed film 4 is a thin film having the thickness of a few μm and formed in such manner that a solvent is prepared from alkane polymer and then the film is applied with the casting method.

The reference electrode 5 comprises a substrate formed from a silver wire 6 coated with a silver chloride film 7 using the known electrolytic method; a salt bridge retaining film 8 provided on the surface of the substrate for stably generating the reference electric potential; and a fixed film 4 formed in the same manner as that of the work electrode.

The salt bridge retaining film 8 is a thin film having the thickness of a few μm. In particular, it is a Nafion film, that is, a perfluoroalkylsulfonic acid film impregnated with potassium chloride, which is formed using the casting method.

A conventional potentiometer 13 is provided between both electrodes so that the platinum black wire 2 of the work electrode 1 and the silver wire 6 of the reference electrode 5 are connected via the potentiometer 13 to configure a galvanic PH meter.

In operation, both electrodes are immersed in a liquid under test for which the PH is to be measured. First, in the work electrode, the liquid under test is penetrated through the fixed film 4. Then, in the plasma polymerized film 3, only hydrogen ion is selectively transmitted therethrough except for any miscellaneous material in the liquid under test (for example, chlorine ion ($Cl^-$), urea, protein, vitamin, etc., if the liquid under test is living body specimen such as urine, saliva, etc.). Accordingly, the hydrogen ion is kept in electrically equilibrium on the surface of the platinum black wire 2. Such "Nernst" response produces an electromotive force depending on the PH value of the liquid under test.

Concurrently with the operation of the work electrode 1, as described above, in the reference electrode 5, the liquid under test is penetrated through the fixed film 4 to the salt bridge retaining film 8. Then, the hydrogen ion in the salt bridge retaining film 8 and the silver chloride film 7 is kept in electrically equilibrium relative to the liquid under test. Accordingly, the constant electric potential not depending on the PH value of the liquid under test is generated in the reference electrode 5, which constant potential is called a reference potential.

Due to migration of plus and minus ions in the liquid under test provided by the reaction of both electrodes there is an electrical coupling produced between both electrodes and any potential difference therebetween is measured by the conventional potentiometer 13. Thus, by using the known PH value calculation formula as well as the known galvanic PH meter, the PH value of the liquid under test can be calculated, depending on the measurement of the potential difference.

Next, a second embodiment of an electrochemical sensor according to the present invention will be described with reference to a galvanic ORP meter.

Figure 2:
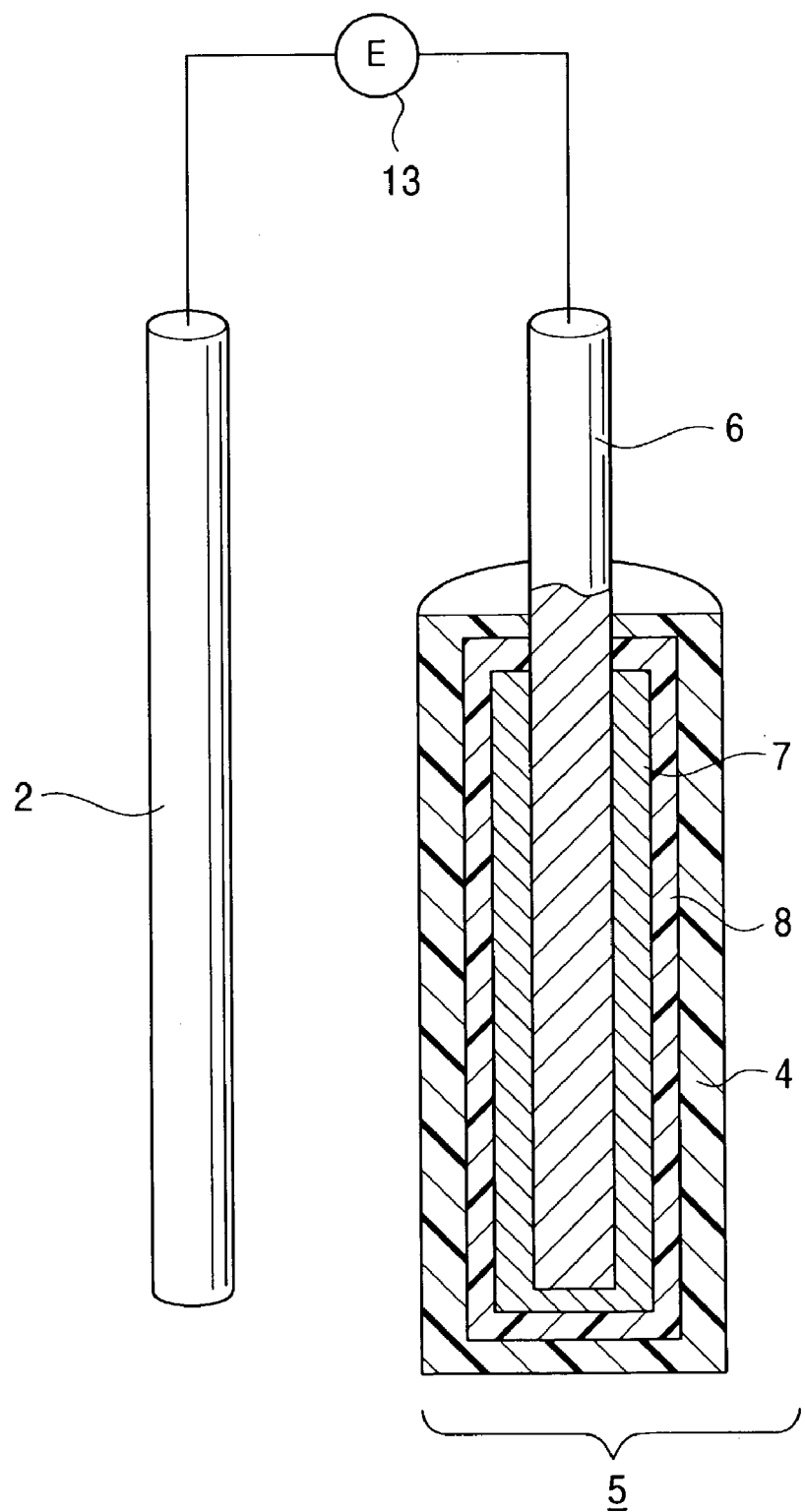
FIG. 2 is a view illustrating an ORP sensor according to a second embodiment of the present invention.

FIG. 2 is a view illustrating an ORP sensor (or a galvanic ORP meter) according to a second embodiment of the present invention. A work electrode comprises a substrate 2 formed from platinum black wire, while a reference electrode 5 is formed in the same manner as that of the first embodiment, as described above. The ORP sensor comprises the work electrode and the reference electrode 5. A conventional potentiometer 13 is provided between both electrodes so that the platinum black wire 2 of the work electrode and the silver wire 6 of the reference electrode 5 are connected via the potentiometer 13 to configure a galvanic ORP meter.

In the work electrode an oxidation-reduction potential is generated due to an oxidation-reduction response, while in the reference electrode a reference potential is generated in the same manner as the first embodiment. The potential difference produced between both electrodes is measured by the conventional potential meter 13. Thus, by using the known ORP value calculation formula as well as the known galvanic ORP meter, the ORP value of the liquid under test can be calculated, depending on the measurement of the potential difference.

Next, a third embodiment of an electrochemical sensor according to the present invention with reference to an integral type PH meter having a work electrode and a reference electrode each mounted on each of opposite sides of an insulation board.

Figure 3:
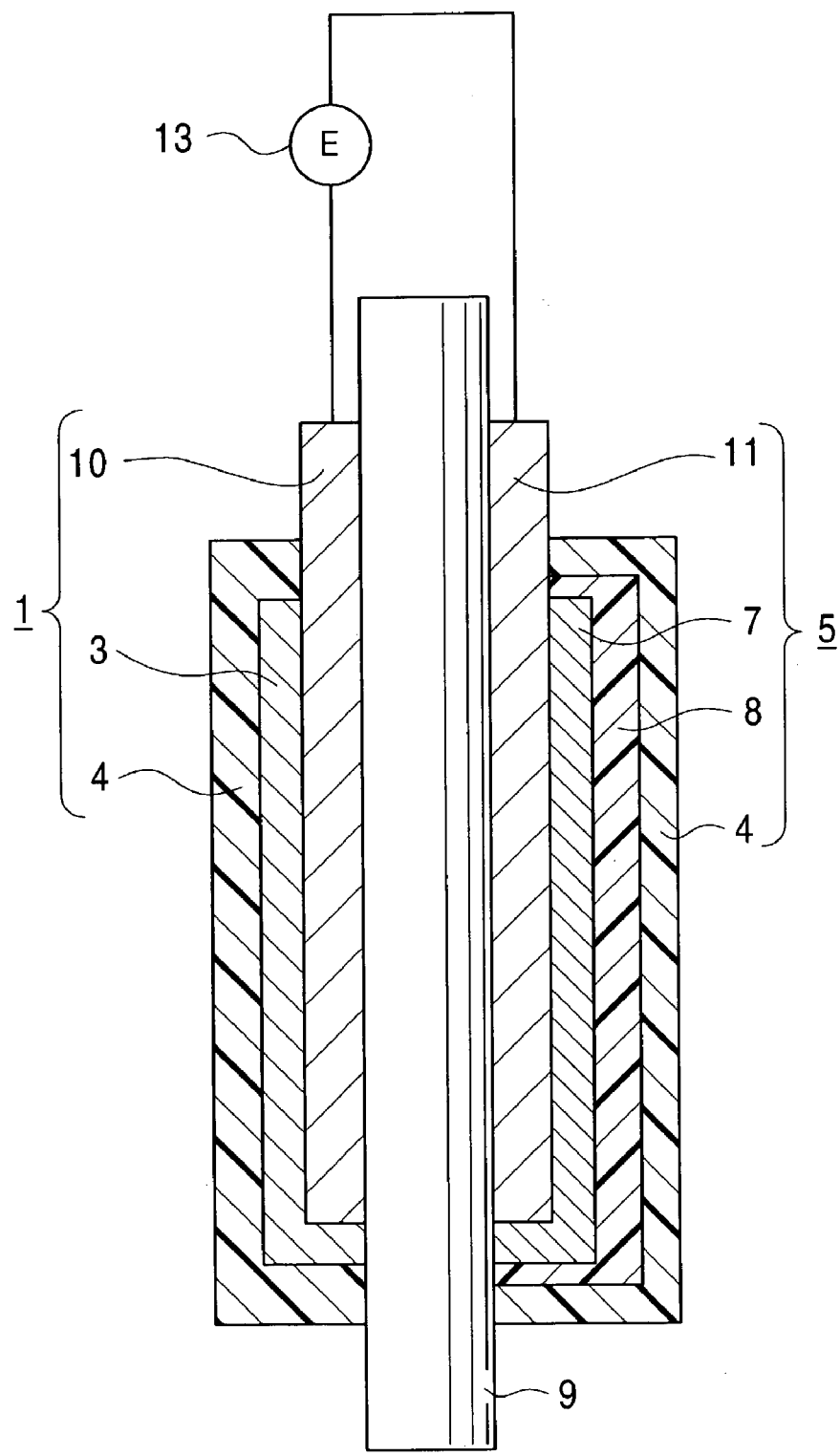
FIG. 3 is a view illustrating an integral type PH sensor according to a third embodiment of the present invention.

FIG. 3 is a view illustrating an integral type PH sensor (or an integral type PH meter). The PH sensor comprises a work electrode 1, a reference electrode 5 and a glass plate (an insulation board) 9. The work electrode 1 comprises a substrate 10 formed from platinum black film provided on one side of the glass plate 9 by an electrolytic method; a plasma polymerized film 3 for covering the surface of the substrate 10; and a fixed film 4 for covering the surface of the plasma polymerized film 3. The reference electrode comprises a substrate formed from a silver film 11 provided on the other side of the glass plate 9 by the electrolytic method and a silver chloride film 7 provided on the silver film 11; a salt bridge retaining film 8 for covering the surface of the substrate; and a fixed film 4 for covering the surface of the salt bridge retaining film 8. A conventional potentiometer 13 is provided between both electrodes so that the platinum black film 10 of the work electrode 1 and the silver film 11 of the reference electrode 5 are connected via the potentiometer 13 to configure an integral type PH meter.

In this embodiment both sides of the glass plate 9 are used, but only one side of the glass plate may be used for forming both electrodes thereon unless they are overlapped. The insulation board is not limited to the glass plate, but any suitable insulation board such as a ceramic board, a resin board, a glass fiber board, etc., may be used.

In the third embodiment as above, the integral type PH meter having the work electrode and the reference electrode each formed on each of opposite sides of the insulation board was described. Next, an additional integral type PH meter having a work electrode and a reference electrode both coaxially formed will be described as a fourth embodiment of an electrochemical sensor according to the present invention.

Figure 4:
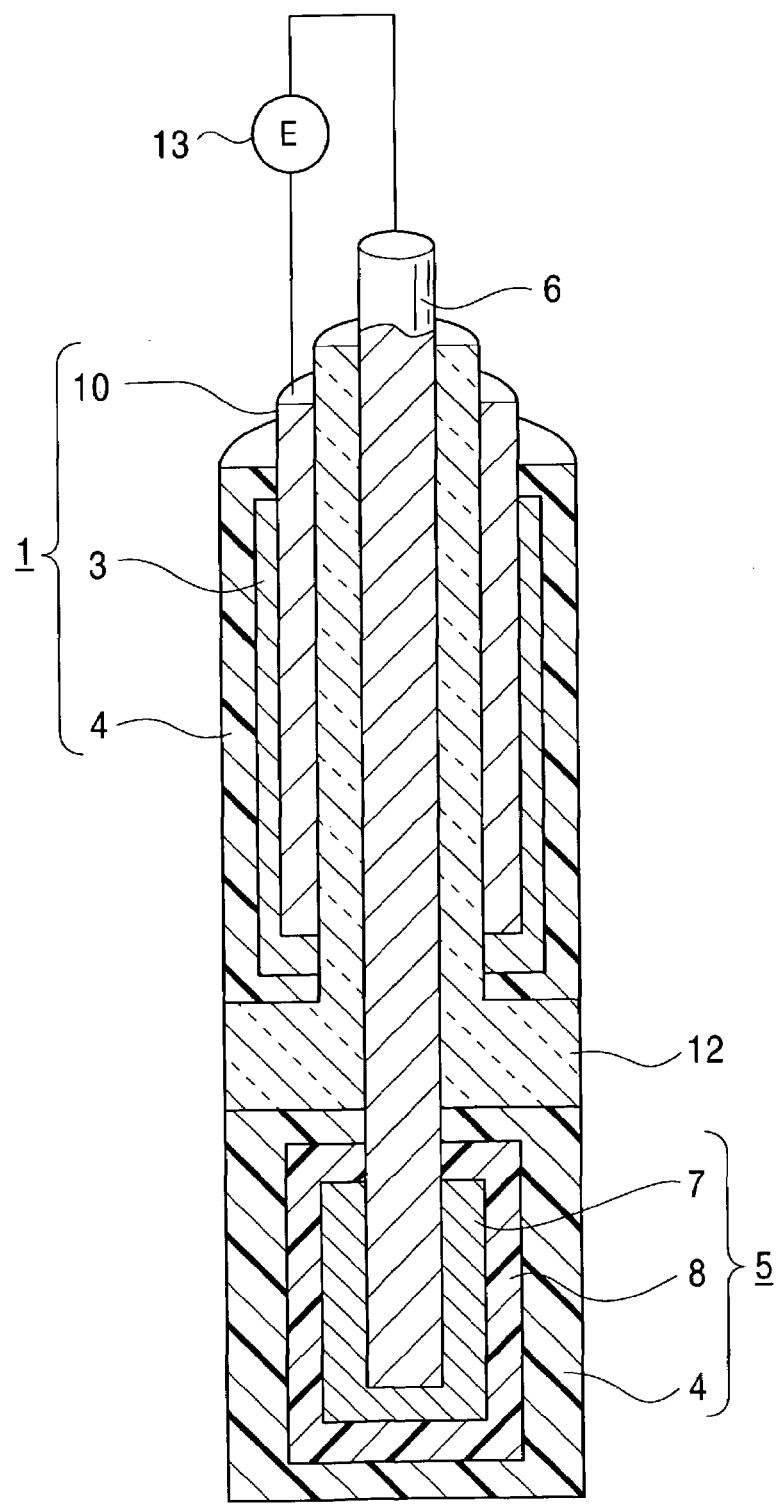
FIG. 4 is a view illustrating an integral type PH sensor according to a fourth embodiment of the present invention.

FIG. 4 is a view illustrating an additional integral type PH sensor (or an integral type PH meter) without the need of any insulation board. The PH sensor comprises a work electrode 1, a reference electrode 5 and a glass section (an insulator) 12. A silver wire 6 forming an axis is coated with a silver chloride film 7 for partially covering any one portion of the silver wire 6, then, a salt bridge retaining film 8 and a fixed film 4 are sequentially provided to form the reference electrode 5. Furthermore, in order to space from the reference electrode 5, the glass section 12 is provided for covering another portion of the silver wire 6. The glass section 12 is sequentially coated with a platinum black film 10, a plasma polymerized film 3 and a fixed film 4 to form the work electrode. A conventional potentiometer 13 is provided between both electrodes so that the platinum black film 10 of the work electrode 1 and the silver film 11 of the reference electrode 5 are connected via the potentiometer 13 to configure an integral type PH meter.

Next, a fifth embodiment of an electrochemical sensor according to the present invention will be described with reference to a PH meter having a reference electrode that is different from that of the first embodiment.

Figure 5:
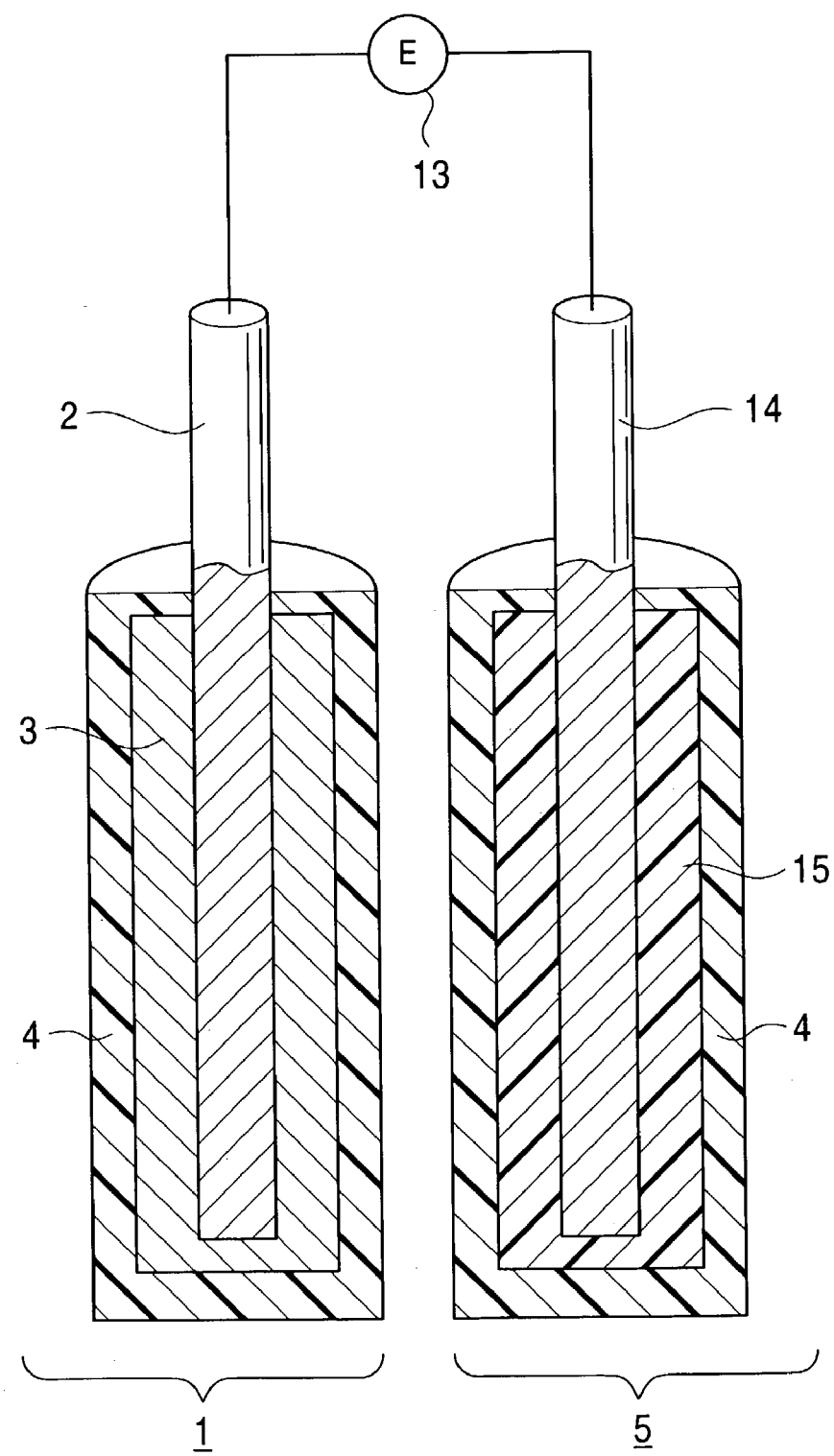
FIG. 5 is a view illustrating a PH meter according to a fifth embodiment of the present invention.

FIG. 5 is a view illustrating a PH meter having a reference electrode that is different from that of the first embodiment. The PH sensor comprises a work electrode 1 and a reference electrode 5. The work electrode 1 has the same configuration as that of the first embodiment. Therefore, the description of the work electrode 1 is omitted.

The reference electrode 5 comprises a substrate 14 formed from a gold wire; a plasma polymerized film 15 having selective material non-transmission capability provided on the surface of the substrate 14; and a fixed hydrophobic film 4 for protecting and stabilizing the plasma polymerized film 15 on the substrate 14.

The plasma polymerized film 15 is a thin film having the thickness of a few tens nm and formed from paraxylene, an aromatic compound, using the plasma polymerization process. The fixed film 4 is a thin film having the thickness of a few μm and formed in such manner that a solvent is prepared from alkane polymer and then the film is applied with the casting method.

A conventional potentiometer 13 is provided between both electrodes so that the platinum black wire 2 of the work electrode 1 and the gold wire 14 of the reference electrode 5 are connected via the potentiometer 13 to configure a galvanic PH meter.

In operation, both electrodes are immersed in a liquid under test for which the PH is to be measured. First, in the reference electrode 5, the liquid under test is penetrated through the fixed film 4. Then, in the plasma polymerized film 15, some components in the liquid under test are selectively not transmitted so that the liquid under test is kept in electrically equilibrium on the surface of the gold wire 14. Accordingly, the constant electric potential (or the reference potential) not depending on the PH value of the liquid under test is generated in the reference electrode 5.

Due to migration of plus and minus ions in the liquid under test provided by the reaction of both electrodes there is an electrical coupling produced between both electrodes and any potential difference therebetween is measured by the conventional potentiometer 13. Thus, by using the known PH value calculation formula, the PH value of the liquid under test can be calculated, depending on the measurement of the potential difference, in the same manner as the first embodiment.

Next, a sixth embodiment of an electrochemical sensor according to the present invention will be described with reference to a PH meter having a reference electrode that is different from that of the first embodiment.

Figure 6:
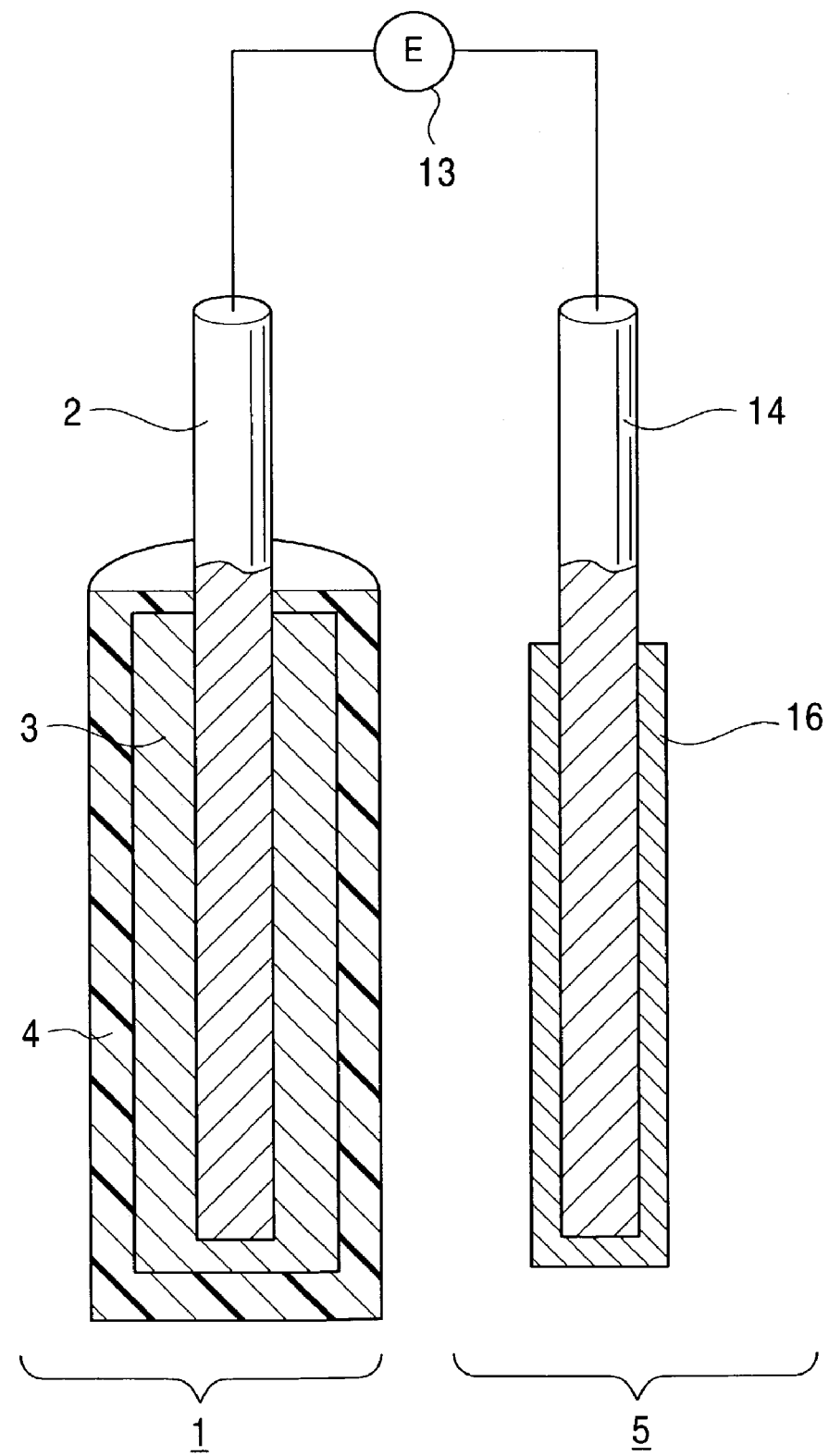
FIG. 6 is a view illustrating a PH meter according to a sixth embodiment of the present invention.

FIG. 6 is a view illustrating a PH meter having a reference electrode that is different from that of the first embodiment. The PH sensor comprises a work electrode 1 and a reference electrode 5. The work electrode 1 has the same configuration as that of the first embodiment. Therefore, the description of the work electrode 1 is omitted.

The reference electrode 5 comprises a substrate 14 formed from a gold wire; and a basic solution immersion film 16 provided on said gold substrate by immersing it in the basic solution such as sodium hydroxide.

A conventional potentiometer 13 is provided between both electrodes so that the platinum black wire 2 of the work electrode 1 and the gold wire 14 of the reference electrode 5 are connected via the potentiometer 13 to configure a galvanic PH meter.

In operation, both electrodes are immersed in a liquid under test for which the PH is to be measured. First, in the reference electrode 5, the liquid under test is penetrated through the basic solution immersion film 16. Then, the liquid under test is kept in electrically equilibrium on the surface of the gold wire 14. Accordingly, the constant electric potential (or the reference potential) not depending on the PH value of the liquid under test is generated in the reference electrode 5.

Due to migration of plus and minus ions in the liquid under test provided by the reaction of both electrodes there is an electrical coupling produced between both electrodes and any potential difference therebetween is measured by the conventional potentiometer 13. Thus, by using the known PH value calculation formula, the PH value of the liquid under test can be calculated, depending on the measurement of the potential difference, in the same manner as the first embodiment.

The present invention has been described above with reference to the first to sixth embodiments, but further embodiment may be possible, as described below:

The silver chloride film 7 in the first to fourth embodiments, as well as the platinum black film 10 of the work electrode 1 and the silver film 11 of the reference electrode 5 in the third to fourth embodiments have been described above as being formed by the electrolytic method. However, the film forming process for those films is not limited to the electrolytic method, but any other method such as non-electrolytic method, sputtering method, ion plating method, foil adhesion method, screen printing due to paste material, direct depiction method using ink-jet, etc., may be used.

For the substrate of the work electrode, the platinum black wire was used in the first and second embodiment, and the platinum black film was used in the third and fourth embodiments. However, any other wires and films such as platinum and gold wires as well as platinum and gold films may be used. In the fifth and sixth embodiments the gold wire was used for the substrate of the work electrode. However, the platinum wire and the platinum black wire may also be used. In addition, a foil or other suitable type member may be used instead of the wire.

The plasma polymerized film 3 has been described above as being formed by the plasma processing of paraxylene, an aromatic compound. However, it may be formed by the plasma processing of at least one of aromatic compound, fluorinated compound and alcohol compound.

The salt bridge retaining film 8 has been described above as being Nafion film, that is, the perfluoroalkylsulfonic acid film impregnated with potassium chloride for the salt bridge. Alternatively, any perfluoroalkylsulfonic acid film impregnated with sodium chloride for the salt bridge may be used. Additionally, the salt bridge retaining film may be a salt bridge crystal film formed in such manner that crystallization of the salt bridge is made on the surface of the substrate for covering the same. Furthermore, the reference electrode has been described above as using the silver coated with the silver chloride for the substrate. However, if a mixture wherein the silver chloride is added to the salt bridge is used to form the salt bridge retaining film, then the silver chloride film 7 of the substrate may be dispensed with.

The fixed film 4 has been described above as being formed from an alkane polymer. However, it may be formed from an annular olefin polymer.

In the embodiments as described above the electrochemical sensor was manufactured in the linear or plate-like form. However, it may be designed in any other form such as cylindrical or foil form as long as the thin films could be formed.

In the sixth embodiment the basic solution immersion film was formed by immersion of the substrate in sodium hydroxide solution. However, it may be formed by immersion in potassium hydroxide solution.

The plasma polymerized film, the salt bridge retaining film and the basic solution immersion film for the work electrode or the reference electrode are not limited to those types as described above, but any other suitable types may be used as long as they intervene between the substrate and the liquid under test for serving to generate an electric potential from the substrate.

The electrochemical sensor of the present invention can be used with any type of the measuring device such as galvanic, polarographic, coulometry, etc., if it is suitable for measuring the relative electric potential or electric current between a pair of electrodes.

It is apparent from the foregoing that in an electrochemical sensor according to the present invention at least one of a work electrode and a reference electrode comprises a substrate coated with a function film for serving to generate an electric potential through the intervention of the film between the substrate and a liquid under test. As the result, the present invention advantageously obviates the need of the internal liquid used in the sensor, makes easy to manufacture and handle the sensor, and allows for miniaturization of the sensor.

Furthermore, in an electrochemical sensor according to the present invention a reference electrode comprises a substrate coated with a function film for serving to generate an electric potential through the intervention of the film between the substrate and a liquid under test. As the result, the present invention advantageously makes easy to manufacture and handle the sensor, and allows for miniaturization of the sensor.

Moreover, the present invention provides an electrochemical sensor for measuring the characteristics of a liquid under test, based on the relative electric potential difference and electric current between a work electrode and a reference electrode both immersed in the liquid under test, said work electrode comprising a substrate formed from platinum, gold, platinum black, etc., and said reference electrode comprising a substrate formed from gold. According to the present invention the reference electrode comprises the gold substrate coated with a plasma polymerized film having selective material non-transmission capability or with a basic solution immersion film. As the result, advantageously the internal liquid is unnecessary and the solidification of the electrode becomes possible. In addition, the precision in measurement is enhanced because of no change in voltage between the liquids. Moreover, handling of the electrochemical sensor is facilitated and miniaturization of the sensor becomes possible.

Furthermore, the present invention provides an electrochemical sensor for measuring the characteristics of a liquid under test, based on the relative electric potential difference and electric current between a work electrode and a reference electrode both immersed in the liquid under test, said work electrode comprising a substrate formed from platinum, gold, platinum black, etc., and said reference electrode comprising a substrate formed from silver coated with silver chloride film. According to the present invention, the reference electrode comprises the substrate coated with a salt bridge retaining film. Such configuration of the present invention advantageously obviates the need of the internal liquid and makes possible for solidification of the electrode. Then, the precision in measurement is enhanced because of no change in voltage between the liquids. In addition, handling of the electrochemical sensor is facilitated and miniaturization of the sensor becomes possible.

In the electrochemical sensor of the present invention the electrode is solidified using the coating of thin films. Therefore, as compared to the electrode using the thin glass film or the liquid catalyst, the internal resistance of the electrode becomes reduced, which obviates need of the amplifier having higher input impedance for increasing the voltage level upon measuring the potential difference. Accordingly, it is possible to measure with an inexpensive measuring device incorporating a common potentiometer.

Furthermore, the work electrode may comprise said substrate coated with a plasma polymerized film having selective material transmission capability and consisting of at least one of aromatic compound, fluorinated compound, alcohol compound, etc. Accordingly, if, for example, paraxylene, an aromatic compound, is applied to the substrate using the plasma polymerization process, it is possible to form a film having the capability of selectively transmitting hydrogen ion. In addition, this plasma polymerized film is advantageous in that it has higher close adhesion to the substrate, it prevents any bubble from mixing or any liquid under test from entering, and it removes any other material than hydrogen ion in the liquid under test. If the combination of said compounds or the condition for plasma polymerization is changed it is possible to form any plasma polymerized film suitable for selectively transmitting any specific material of each type. Alternatively, if a plurality of plasma polymerized films each having different characteristic are formed in parallel on the substrate, a plurality of liquid characteristics may be measured.

The work electrode and the reference electrode may be coated with a fixed hydrophobic film consisting of alkane polymer and annular olefin polymer. In such case, because of suppression in peering of thin film and increase in strength, the service life of the electrode is extended.

Furthermore, the substrates of the work electrode and the reference electrode may integrally be configured on the surface of an insulation board so as not to contact to each other. Therefore, further miniaturization of the electrochemical sensor of the present invention may be possible. In addition, because of close proximity of both electrodes, the internal resistance in the measuring system is minimized.

Moreover, the salt bridge retaining film may be a perfluoroalkylsulfonic acid film impregnated with potassium chloride, sodium chloride, etc., as the salt bridge or may be a salt bridge crystal film formed by crystallization of salt bridge of potassium chloride, sodium chloride, etc. In this case, any thin film retaining the salt bridge therein reaches an electrical equilibrium with the liquid under test through chlorine ion in salt bridge in the thin film. Accordingly, the liquid under test is prevented from contacting to the substrate for erosion thereto, which makes possible to extend the service life of the sensor.

Furthermore, the salt bridge may be a mixture to which silver chloride is further added. In such case, the substrate may simply be formed from silver without any silver chloride coating.

What is claimed is:

1. An electrochemical sensor comprising a work electrode and a reference electrode, said sensor adapted to measure the characteristics of a liquid under test, based on the relative electric potential difference and electric current between the work electrode and the reference electrode both immersed in the liquid under test, said work electrode having a substrate comprising at least one of platinum, gold, and platinum black, and said reference electrode having a substrate comprising gold;

wherein said reference electrode substrate is coated with a function film for serving to generate the electric potential through the intervention of the film between said substrate and the liquid under test; and wherein said reference electrode comprises a basic solution immersion film provided on said reference electrode substrate as said function film by immersing the reference electrode substrate in a basic solution comprising sodium hydroxide or potassium hydroxide.

2. An electrochemical sensor according to claim 1 wherein said work electrode comprises a plasma polymerized film having selective material transmission capability provided on said substrate, said plasma polymerized film consisting of at least one of an aromatic compound, a fluorinated compound, and an alcohol compound.

3. An electrochemical sensor according to claim 2 wherein said selective material transmission capability for said plasma polymerized film of the work electrode provides selective transmission of hydrogen ion.

4. An electrochemical sensor according to claim 2 wherein said work electrode and said reference electrode are coated with a fixed hydrophobic film consisting of alkane polymer and annular olefin polymer.

5. An electrochemical sensor according to claim 1 wherein said work electrode and said reference electrode are coated with a fixed hydrophobic film consisting of alkane polymer and annular olefin polymer.

6. An electrochemical sensor comprising a work electrode and a reference electrode, said sensor adapted to measure the characteristics of a liquid under test, based on the relative electric potential difference and electric current between the work electrode and the reference electrode both immersed in the liquid under test, said work electrode having a substrate comprising at least one of platinum, gold, and platinum black, and said reference electrode having a substrate comprising silver coated with silver chloride film;

wherein said reference electrode substrate is coated with a function film for serving to generate the electric potential through the intervention of the film between said reference electrode substrate and the liquid under test;

wherein said reference electrode comprises a salt bridge retaining film provided on said reference electrode substrate as said function film;

wherein said work electrode comprises a plasma polymerized film having selective material transmission capability provided on said work electrode substrate, said plasma polymerized film consisting of at least one of an aromatic compound, a fluorinated compound, and an alcohol compound; and wherein said work electrode and said reference electrode are coated with a fixed hydrophobic film consisting of alkane polymer and annular olefin polymer.

7. An electrochemical sensor comprising a work electrode and a reference electrode, said sensor adapted to measure the characteristics of a liquid under test, based on the relative electric potential difference and electric current between the work electrode and the reference electrode both immersed in the liquid under test, said work electrode having a substrate comprising at least one of platinum, gold, and platinum black, and said reference electrode having a substrate comprising silver coated with silver chloride film;

wherein said reference electrode substrate is coated with a function film for serving to generate the electric potential through the intervention of the film between said reference electrode substrate and the liquid under test;

wherein said reference electrode comprises a salt bridge retaining film provided on said reference electrode substrate as said function film; and wherein said work electrode and said reference electrode are coated with a fixed hydrophobic film consisting of alkane polymer and annular olefin polymer.

8. An electrochemical sensor comprising a work electrode and a reference electrode, said sensor adapted to measure the characteristics of a liquid under test, based on the relative electric potential difference and electric current between the work electrode and the reference electrode both immersed in the liquid under test, said work electrode having a substrate comprising at least one of platinum, gold, and platinum black, and said reference electrode having a substrate comprising gold;

wherein said reference electrode substrate is coated with a function film for serving to generate the electric potential through the intervention of the film between said reference electrode substrate and the liquid under test;

wherein said reference electrode comprises a plasma polymerized film having selective material non-transmission capability provided on said gold reference electrode substrate as said function film, said plasma polymerized film consisting of at least one of an aromatic compound, a fluorinated compound, and alcohol compound;

wherein said work electrode comprises a plasma polymerized film having selective material transmission capability provided on said work electrode substrate, said plasma polymerized film consisting of at least one of an aromatic compound, a fluorinated compound, and an alcohol compound; and wherein said work electrode and said reference electrode are coated with a fixed hydrophobic film consisting of alkane polymer and annular olefin polymer.

9. An electrochemical sensor comprising a work electrode and a reference electrode, said sensor adapted to measure the characteristics of a liquid under test, based on the relative electric potential difference and electric current between the work electrode and the reference electrode both immersed in the liquid under test, said work electrode having a substrate comprising at least one of platinum, gold, and platinum black, and said reference electrode having a substrate comprising gold;

wherein said reference electrode substrate is coated with a function film for serving to generate the electric potential through the intervention of the film between said reference electrode substrate and the liquid under test;

wherein said reference electrode comprises a plasma polymerized film having selective material non-transmission capability provided on said gold reference electrode substrate as said function film, said plasma polymerized film consisting of at least one of an aromatic compound, a fluorinated compound, and alcohol compound; and wherein said work electrode and said reference electrode are coated with a fixed hydrophobic film consisting of alkane polymer and annular olefin polymer.

10. An electrochemical sensor comprising a work electrode and a reference electrode, said sensor adapted to measure the characteristics of a liquid under test, based on the relative electric potential difference and electric current between the work electrode and the reference electrode both immersed in the liquid under test, said work electrode having a substrate comprising at least one of platinum, gold, and platinum black, and said reference electrode having a substrate comprising silver coated with silver chloride film, or comprising gold, wherein said reference electrode substrate is coated with a function film for serving to generate the electric potential through the intervention of the film between said reference electrode substrate and the liquid under test;

wherein said work electrode comprises a plasma polymerized film having selective material transmission capability provided on said work electrode substrate, said plasma polymerized film consisting of at least one of an aromatic compound, a fluorinated compound, and an alcohol compound; and wherein said work electrode and said reference electrode are coated with a fixed hydrophobic film consisting of alkane polymer and annular olefin polymer.

11. An electrochemical sensor comprising a work electrode and a reference electrode, said sensor adapted to measure the characteristics of a liquid under test, based on the relative electric potential difference and electric current between the work electrode and the reference electrode both immersed in the liquid under test, said work electrode having a substrate comprising at least one of platinum, gold, and platinum black, and said reference electrode having a substrate comprising silver coated with silver chloride film, or comprising gold, wherein said reference electrode substrate is coated with a function film for serving to generate the electric potential through the intervention of the film between said reference electrode substrate and the liquid under test;

wherein said work electrode and said reference electrode are coated with a fixed hydrophobic film consisting of alkane polymer and annular olefin polymer.

12. An electrochemical sensor according to claim 11 wherein said work electrode and said reference electrode are integrally assembled, but insulated from each other.

13. An electrochemical sensor comprising a work electrode and a reference electrode, said sensor adapted to measure the characteristics of a liquid under test, based on the relative electric potential difference and electric current between the work electrode and the reference electrode both immersed in the liquid under test, said work electrode having a substrate comprising at least one of platinum, gold, and platinum black, and said reference electrode having a substrate comprising silver coated with silver chloride film;

wherein said reference electrode substrate is coated with a function film for serving to generate the electric potential through the intervention of the film between said reference electrode substrate and the liquid under test;

wherein said reference electrode comprises a salt bridge retaining film provided on said reference electrode substrate as said function film; and wherein said salt bridge retaining film is a perfluoroalkyl-sulfonic acid film impregnated with a salt bridge comprising potassium chloride or sodium chloride.

14. An electrochemical sensor according to claim 13 wherein said salt bridge is a mixture to which silver chloride is further added.

* * * * *